United States Patent [19]

Bowers

[11] Patent Number: 4,542,150

[45] Date of Patent: Sep. 17, 1985

[54] ANTI-JUVENILE HORMONES

[75] Inventor: William S. Bowers, Geneva, N.Y.

[73] Assignee: Cornell Research Foundation, Inc., Ithaca, N.Y.

[21] Appl. No.: 239,744

[22] Filed: Mar. 2, 1981

Related U.S. Application Data

[63] Continuation-in-part of Ser. No. 739,886, Nov. 8, 1976, which is a continuation-in-part of Ser. No. 613,991, Sep. 17, 1975, abandoned.

[51] Int. Cl.$^4$ ................... A01N 43/08; C07D 311/02
[52] U.S. Cl. .................................. 514/456; 514/454; 549/389; 549/406
[58] Field of Search ................. 424/285; 260/345.2, 260/345.3; 549/406

[56] References Cited

U.S. PATENT DOCUMENTS

| | | | |
|---|---|---|---|
| 3,004,040 | 10/1961 | Pendse et al. | 260/345.2 |
| 3,725,551 | 4/1973 | Bowers | 424/282 |
| 3,957,763 | 5/1976 | Chodnekar | 260/240 R |
| 4,029,811 | 6/1977 | Tamagnone et al. | 424/285 |
| 4,048,317 | 4/1977 | Watts | 424/267 |
| 4,110,347 | 8/1978 | Watts | 260/345.2 |
| 4,162,326 | 7/1978 | Mihailovski | 424/285 |
| 4,167,515 | 9/1979 | Gardner | 260/345.2 |

OTHER PUBLICATIONS

G. T. Brooks et al., "Proceedings 1979 British Crop Protection Conference—Pests And Diseases", pp. 273–277.

Natural Products Protection Of Plants, Elsevier Scientific Publishing Company, New York, 1977.

*Primary Examiner*—Leonard Schenkman

[57] ABSTRACT

Potential insect control compounds which are chromenes, as well as their method of preparation and use, are disclosed. Compounds have been found which are effective in the control of insects by inhibiting the actions of juvenile hormone. An example of a useful compound is 5-methyl-7-ethoxy-2,2-dimethyl-3-chromene. Such compounds act to induce precocious maturation of immature insects, resulting in death either during or within a short time before or after the molting to an incompetant precocious adult. Additional effects which have been obtained include sterilization of mature insects.

21 Claims, No Drawings

ANTI-JUVENILE HORMONES

RELATED APPLICATION

This application is a continuation-in-part of Ser. No. 739,886, filed Nov. 8, 1976, which in turn is a continuation-in-part of application Ser. No. 613,991, filed Sept. 17, 1975 now abandoned.

BACKGROUND AND SUMMARY OF THE INVENTION

The present invention is directed to compounds potentially useful in controlling insects. More particularly, the present invention is directed to active chromene compounds which are effective in inhibiting the effects of juvenile hormone in insects.

Of the various chemical compounds which have been employed in the prior art as insecticides for controlling insects, many of such prior art compounds have also been found to be harmful to humans and other animal life. In addition, many species of insect pests have developed a resistance and even immunity to available insecticides.

Alternative prior art methods for controlling insects have included the use of hormones, which interfere with the development of insects. Although such hormones have the advantage of apparently being harmless to other animals, their use is generally limited to application relatively late in the insect life cycle, after the insect has already produced its undesirable pest effect.

The endocrine systems of insects secrete a certain hormone known as juvenile hormone which functions to control the biological activities of metamorphosis, reproduction, diapause and sex attractant production. In particular, juvenile hormone functions initially to maintain the young developing insect in an immature condition until it has developed to the point where it is ready to molt to the adult form. When maturation of the insect begins, the body ceases to secrete juvenile hormone until after the insect has passed into the adult form, at which time secretion of juvenile hormone recommences in order to promote the development of the sex organs.

The forms in which juvenile hormone are known to occur in nature are discussed in the following publications: Trautmann et al., Z. Naturforsch, 29C 161-168 (1974); Judy et al., Proc. Nat. Acad. Sci. USA, 70, 1509-1513 (1973); Roller et al., Angew. Chem. Int. Ed. Eng., 6, 179-180 (1967); Meyer et al., Proc. Nat. Acad. Sci. USA, 60, 853-860 (1968); Judy et al., Life Sci., 13, 1511-1516 (1973); Jennings et al., Life Sci., 16, 1033-1040 (1975); and Judy et al., Life Sci., 16, 1059-1066 (1975).

In accordance with the present invention, it has been discovered that the lipid extract of the common bedding plant, Ageratum, contains two active compounds: (1) 6,7-dimethoxy-2-,2-dimethyl-3-chromene; and (2) 7-methoxy-2,2-dimethyl-3-chromene; each of which is effective to inhibit the effects of juvenile hormone in insects. Both compounds have been described in the literature: A. R. Alertsen "Ageratochromene, a Heterocyclic Compound from the Essential Oils of some Agertaum Species", Acta Chem. Scand. 9 (1955) No. 10, pp. 1725-1726; R. Huls "Syntheses De Chromenes Substitutes", Bull. Soc. Chim. Belg., 67 (1958), pp. 22-32; R. Livingston et al., J. Chem. Soc., p. 1509 et seq. (1957); and T. R. Kasturi et al., Tetrahedron Lett., 27 (1967), p. 2573 et seq.

These and related chromene compounds inhibit the effects of juvenile hormone, during early development of the insect and after reaching adulthood when the sex organs are undergoing development. By so inhibiting the effects of juvenile hormone, the maturing insect which has been treated with the present compounds is caused to die within a short time of such treatment. In addition, the ability of a treated insect to reproduce is prevented. The compounds of the present invention are also believed capable of interrupting embryogenesis in insect eggs, inducing diapause in insects and preventing sex pheromone secretion in insects. The present compounds may be applied by suitable means including topically, orally or in a vapor state as a fumigant.

As set forth in application Ser. No. 739,886, filed Nov. 8, 1976, based upon the activity of the extracts of Agertaum, compounds potentially suitable for use as antijuvenile hormones are selected from those with the following general structure of Formula I

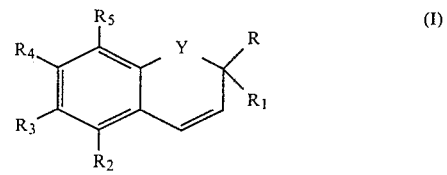

wherein:

R and $R_1$ are H, lower alkyl, straight or branched chain, of about 1 to 4 carbon atoms, lower alkoxy, straight or branched chain, of about 1 to 3 carbon atoms, Cl, Br or F;

$R_2$, $R_3$, $R_4$ and $R_5$ are H, lower alkyl, straight or branched chain, of 1 to 6 carbon atoms, lower alkoxy, straight or branched chain, of 1 to 6 carbon atoms, OH, $-OCH_2OCH_3$, $-OC_2H_4OC_2H_5$, $-CO-OCH_3$, $-CO-OCH_2CH_3$,

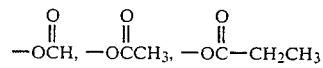

Cl, Br, F, $-SCH_3$, $-SCH_2CH_3$, $-SCH_2CH_2CH_3$, $-NO_2$, or the structure wherein $R_2$ and $R_3$, or $R_3$ and $R_4$, or $R_4$ and $R_5$ are joined with a $-OCH_2O-$ (methylenedioxy) group; or $-OCH_2CH_2-$ (ethylenedioxy) group and Y is O, S or NH.

DESCRIPTION OF THE INVENTION

It has been further found that a particular group of compounds potentially suitable for use as anti-juvenile hormones comprises compounds corresponding to the formulae:

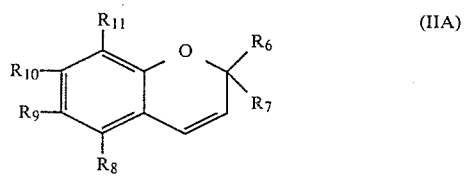

wherein:

$R_6$ and $R_7$ are each hydrogen, or straight or branch chain lower alkyl containing 1–4 carbon atoms, preferably $R_6$ and $R_7$ both being methyl;

$R_8$, $R_9$, $R_{10}$ and $R_{11}$ are each hydrogen, straight or branch chain lower alkyl, alkenyl, alkoxy, or alkenoxy or alkynoxy containing 1–4 carbon atoms;

provided that at least one of $R_9$ and $R_{10}$, preferably $R_{10}$, is lower alkoxy or alkenoxy containing 1–4 carbon atoms;

and further provided that at least one of $R_8$ and $R_{11}$ is hydrogen, straight or branch chain lower alkyl, alkenyl, alkoxy, alkynoxy, or alkenoxy containing 1–4 carbon atoms;

or provided that $R_{10}$ is lower alkoxy or alkenoxy containing 1–4 carbon atoms and at least one of $R_8$, $R_9$ and $R_{11}$ is phenyl;

or provided that $R_{10}$ is lower alkoxy or alkenoxy containing 1–4 carbon atoms and $R_9$ is lower alkyl containing 1–4 carbon atoms, preferably ethyl;

or

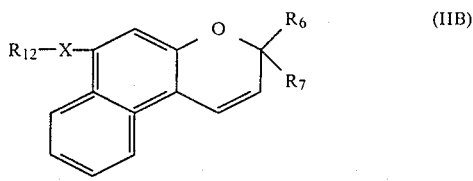

(IIB)

where $R_6$ and $R_7$ are hydrogen or straight or branch chain lower alkyl containing 1–4 carbon atoms, preferably both $R_6$ and $R_7$ being methyl; X is O, S or N and $R_{12}$ is alkyl or alkenyl containing 1–4 carbon atoms or

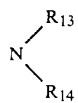

where $R_{13}$ and $R_{14}$ are methyl or ethyl.

Examples of such compounds include:
5-methyl-7-ethoxy-2,2-dimethyl-3-chromene
5-methyl-7-methoxy-2,2-dimethyl-3-chromene
7-ethoxy-6-methoxy-5-methyl-2,2-dimethyl-3-chromene
6,7-dimethoxy-5-methyl-2,2-dimethyl-3-chromene
7-ethoxy-8-methyl-2,2-dimethyl-3-chromene
7-methoxy-8-methyl-2,2-dimethyl-3-chromene
6,7-dimethoxy-8-methyl-2,2-dimethyl-3-chromene
7-ethoxy-6-ethyl-2,2-dimethyl-3-chromene
7-methoxy-6-ethyl-2,2-dimethyl-3-chromene
7-ethoxy-6-methyl-2,2-dimethyl-3-chromene The present invention also relates to a process for the manufacture of compounds of the above formula, which process comprises reacting a compound of the general Formula III:

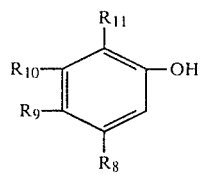

(III)

wherein:

$R_8$, $R_9$, $R_{10}$, and $R_{11}$ are substituents given in Formula II, with a compound of the general Formula IV:

(IV)

wherein, in Formula IV:
X is H, OH, Cl, Br or I; and
$R_6$ and $R_7$ are as given in connection with Formula II; in the presence of a Friedel-Crafts catalyst such as formic acid, methansulfonic acid, $AlCl_3$, $ZnCl_2$, polyphosphoric acid, $SnCl_4$ or other similar catalyst well known in the art. A suitable solvent which is compatible with the Friedel-Crafts catalyst may be employed as necessary. Such a solvent may be, for example, ether, nitrobenzene or carbon disulfide. The reaction produces a chromanone of the general Formula V:

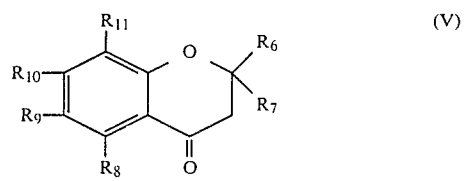

(V)

wherein the substituents are those given with regard to Formula II. The addition of heat, by means such as conducting the reaction on a steam bath for one to several hours, may be employed although such heating is not always necessary for obtaining the chromanone product.

The compounds of Formula V are reduced with a reducing agent which may be any of those well known to one skilled in the art, such as lithium aluminum hydride or sodium borohydride, in a suitable solvent such as tetrahydrofuran or ether, to give a chromanol of the general Formula VI:

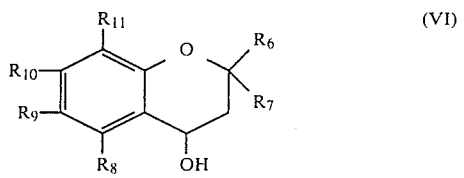

(VI)

wherein the substituents are those given in connection with Formula II. If, following reduction, the reduction mixture containing the compounds of Formula VI are treated with a dilute acid such as hydrochloric, toluenesulfonic or other similar acid well known to those skilled in the art, dehydration of the hydroxyl group occurs given the chromenes directly corresponding to the compounds given in connection with Formula II. When the chromanols are isolated directly, subsequent treatment with catalytic amount of acid such as toluenesulfonic in refluxing benzene causes dehydration to the chromene.

In the case of the reaction of the compounds of general Formula III with unsaturated aldehydes of Formula IV in the presence of Friedel-Crafts catalysts, the desired chromenes are produced directly.

In alternative procedures, a compound having the structure of Formula III is reacted with one of the following:

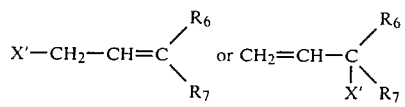

where $R_6$ and $R_7$ have the meaning specified above and X' is a halogen or hydroxyl group. The chromane resulting from this reaction is then dehydrogenated by conventional techniques to give the corresponding chromene.

The following specific examples further illustrate the preparation and utility of compounds within the scope of the general structure II above, and are to be considered illustrative and not limiting. All parts and percentages are by weight unless otherwise specified. All temperatures are degrees Centigrade unless otherwise specified.

EXAMPLE 1

Synthesis of 5-methyl-7-ethoxy-2,2-dimethyl-3-chromene 3 grams of 1,5-dihydroxy-3-methylbenzene are admixed with 3 grams of dimethylacrylic acid. There was then added 20 ml. of methanesulfonic acid and the mixture stirred for 1 hour at 70° C. The mixture was cooled and extracted with ether. The ether solution was washed twice with a saturated aqueous sodium bicarbonate solution and once with a saturated sodium chloride solution. The ether layer was dried over sodium sulfate and then evaporated to yield the corresponding 7-hydroxy-5-methylchromanone (4.5 g).

The above reaction product was dissolved in 40 ml. of dimethylformamide and there was then added 1.3 grams of powdered potassium hydroxide and the mixture stirred for 30 minutes. There was then added 17 grams of ethyl iodide and the mixture stirred overnight. The reaction mixture was then extracted with hexane and the hexane was then washed twice with 10% potassium hydroxide and once with a saturated salt solution. The hexane solution was then dried over sodium sulfate and evaporated to yield the corresponding 7-ethoxy-5-methyl-chromanone (5 g.).

The above reaction product was dissolved in 50 ml. of dry ether and there was then added 0.9 grams of lithium aluminum hydride and the mixture refluxed for 2 hours. The reaction mixture was cooled and excess hydride destroyed by addition of water. 50 ml. of 4NHCl was added and the mixture stirred for 5 minutes. The reaction mixture was washed once with water and once with a saturated salt solution and then dried over sodium sulfate. Upon evaporation 4.3 grams of a product comprising 5-methyl-7-ethoxy-2,2-dimethylchromene was recovered.

Induction of Precocious Development

In accordance with the present invention, active appropriately substituted chromene compounds were found to cause precocious maturation when applied to an immature insect. The juvenile hormone (JH) is a natural insect hormone which acts to keep the developing insect immature until it is ready to molt to the adult form. When maturation of the insect begins, the insect ceases to produce JH and the insect matures to the adult form. The compounds of the present invention have been found to stop the action of JH and cause the immature insect to undergo precocious maturation. For some insects the induced lack of JH causes such rapid maturation that the immature insect dies shortly prior to, or during the molting process. In other insects the lack of JH causes them to molt into miniature adults which completely avoids the tremendous feeding potential of the immature stages and results in tiny adults which are sterile, very fragile and which die soon after molting. The anti-juvenile hormone action can be overcome by the application of exogenous juvenile hormone, which indicates that the anti-juvenile hormone compounds act by interfering with the production of juvenile hormones.

Table I illustrates the induction of precocious maturation by contacting the milkweed bug with a chromene in accordance with the present invention. Other Hemiptera are also quite sensitive, and precocious metamorphosis has been induced in *Lygaeus kalmii* Stal and in *Dysdercus cingulatus*. Satisfactory results have not been obtained in inducing precocious metamorphosis in Holometabola.

Sterilization

In the normal adult insect, JH (or gonadotropic hormone) is produced again after molting to the adult form and is then necessary for the development of the insect ovaries. Treatment of adult insects with the compounds as described below in Table I was found to prevent or stop the action of JH and the insect ovaries failed to develop. If the insect ovaries were developed at the time of treatment, they rapidly regressed to the undeveloped state. In either event, reproduction was prevented. This technique has been successful with insects in the orders Hemiptera, Homoptera, and Orthoptera.

| TABLE 1 | | | | |
|---|---|---|---|---|
| | Induction of Precocious Metamorphosis in Immature Milkweed Bugs *Oncopeltus fasciatus*[1] | | Sterilization of Adult Milkweed Bugs[2] | |
| | Dose ($\mu g/cm^2$) | % Precocious Adults | Dose ($\mu g/cm^2$) | % Sterile |
| [structure: CH$_3$CH$_2$O-, CH$_3$, CH$_3$, CH$_3$ substituted chromene] | 1.5 | 90 | 7.5 | 100 |
| | 0.75 | 50 | | |

TABLE 1-continued

| | Induction of Precocious Metamorphosis in Immature Milkweed Bugs Oncopeltus fasciatus[1] | | Sterilization of Adult Milkweed Bugs[2] | |
|---|---|---|---|---|
| | Dose ($\mu g/cm^2$) | % Precocious Adults | Dose ($\mu g/cm^2$) | % Sterile |
| 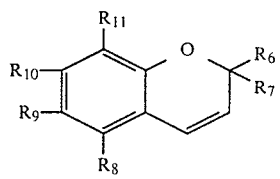 | 3.9 | 75 | 15.0 | 50 |
| 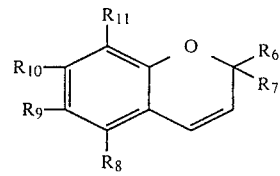 | 1.5 | 100 | 7.5 | 100 |

[1]Second instar nymphs were confined to a 9 cm. petri dish containing a residue of the test compound.

[2]Newly emerged adult female milkweed bugs were confined to a 9 cm. petri dish containing a residue of the test compound for 24 hours and then transferred to an untreated dish and held for 5 days at which time they were autopsied and the status of various development determined.

What is claimed is:

1. A method of treating an insect to inhibit juvenile hormone activity in said insect and thereby effect insect control which comprises contacting an insect with an active anti-juvenile hormone corresponding to the formulae:

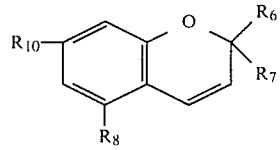

wherein
   $R_6$ and $R_7$ are each hydrogen, or straight or branch chain lower alkyl containing 1-4 carbon atoms; and
   $R_8$, $R_9$, $R_{10}$ and $R_{11}$ are each hydrogen, straight or branch chain lower alkyl, alkenyl, alkoxy, alkynoxy or alkenoxy containing 1-4 carbon atoms;
   provided that at least one of $R_9$ and $R_{10}$ is lower alkoxy or alkenoxy containing 1-4 carbon atoms;
   and further provided that at least one of $R_8$ and $R_{11}$ is straight or branch chain lower alkyl, alkenyl, alkoxy alkynoxy or alkenoxy containing 1-4 carbon atoms;
   or provided that $R_{10}$ is lower alkoxy or alkenoxy containing 1-4 carbon atoms and at least one of $R_8$, $R_9$ and $R_{11}$ is phenyl;
   or provided that $R_{10}$ is lower alkoxy or alkenoxy containing 1-4 carbon atoms and $R_9$ is lower alkyl containing 1-4 carbon atoms.

2. The method as in claim 1 where $R_6$ and $R_7$ are both methyl.

3. The method as in claims 1 or 2 where $R_{10}$ is lower alkoxy or alkenoxy.

4. The method as in claim 1 of treating an insect to inhibit the juvenile hormone activity in said insect and thereby effect insect control which comprises contacting an insect with an active anti-juvenile hormone corresponding to the formula:

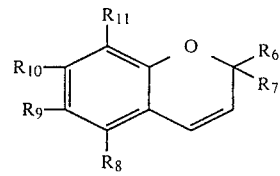

where $R_6$ and $R_7$ are hydrogen or straight or branched chain lower alkyl containing 1-4 carbon atoms and where at least one of $R_9$ and $R_{10}$ is lower alkyl alkoxy, alkenoxy or alkynoxy containing 1-4 carbon atoms, while at least one of $R_8$ and $R_{11}$ is straight or branch chain lower alkyl, alkenyl, alkoxy, alkenoxy or alkynoxy containing 1-4 carbon atoms.

5. The method as in claim 1 wherein the active anti-juvenile hormone corresponds to the formula:

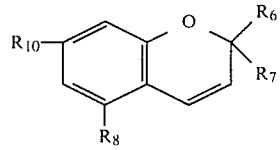

where $R_{10}$ is alkoxy.

6. The method as in claim 1 wherein the active anti-juvenile hormone corresponds to the formula:

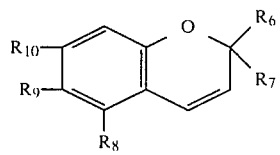

where $R_9$ and $R_{10}$ are alkoxy.

7. The method as in claim 1 wherein the active anti-juvenile hormone corresponds to the formula:

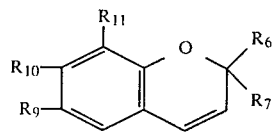

where $R_9$ and $R_{10}$ are alkoxy and $R_{11}$ is alkyl.

8. The method as in claim 1 wherein the active anti-juvenile hormone corresponds to the formula:

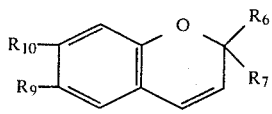

where $R_9$ is alkyl and $R_{10}$ is alkoxy.

9. The method as in claim 1 wherein the active juvenile hormone corresponds to the formula:

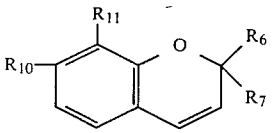

where $R_{10}$ is alkoxy and $R_{11}$ is alkyl.

10. The method as in claims 4, 5, 6, 7, 8 or 9 wherein $R_6$ and $R_7$ are methyl.

11. An active anti-juvenile hormone corresponding to the formulae:

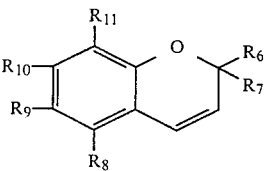

wherein
$R_6$ and $R_7$ are each hydrogen, or straight or branch chain lower alkyl containing 1-4 carbon atoms; and
$R_8$, $R_9$, $R_{10}$ and $R_{11}$ are each hydrogen, straight or branch chain lower alkyl, alkenyl, alkoxy alkynoxy or alkenoxy containing 1-4 carbon atoms;
provided that at least one of $R_9$ and $R_{10}$ is lower alkoxy or alkenoxy containing 1-4 carbon atoms;
and further provided that at least one of $R_8$ and $R_{11}$ is straight or branch chain lower alkyl, alkenyl, alkoxy alkynoxy or alkenoxy containing 1-4 carbon atoms;
or provided that $R_{10}$ is lower alkoxy or alkenoxy containing 1-4 carbon atoms and at least one of $R_8$, $R_9$ and $R_{11}$ is phenyl;
or provided that $R_{10}$ is lower alkoxy or alkenoxy containing 1-4 carbon atoms and $R_9$ is lower alkyl containing 1-4 carbon atoms.

12. The compound as in claim 11 where $R_6$ and $R_7$ are both methyl.

13. The compound as in claims 11 or 12 where $R_{10}$ is lower alkoxy or alkenoxy.

14. The compound as in claim 11 corresponding to the formula:

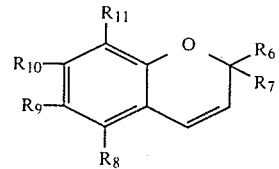

where $R_6$ and $R_7$ are hydrogen or straight or branched chain lower alkyl containing 1-4 carbon atoms; and where at least one of $R_9$ and $R_{10}$ is lower alkoxy, alkenoxy or alkynoxy containing 1-4 carbon atoms, while at least one of $R_8$ and $R_{11}$ is straight or branch chain lower alkyl, alkenyl, alkoxy, alkenoxy or alkynoxy containing 1-4 carbon atoms.

15. The compound as in claim 11 wherein the active anti-juvenile hormone corresponds to the formula:

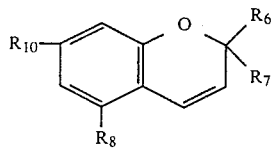

where $R_{10}$ is alkoxy.

16. The compound as in claim 11 wherein the active anti-juvenile hormone corresponds to the formula:

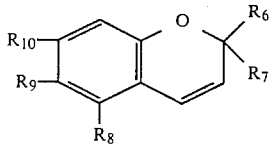

where $R_9$ and $R_{10}$ are alkoxy.

17. The compound as in claim 11 wherein the active anti-juvenile hormone corresponds to the formula:

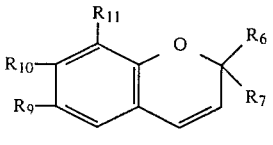

where $R_9$ and $R_{10}$ are alkoxy and $R_{11}$ is alkyl.

18. The compound as in claim 11 wherein the active anti-juvenile hormone corresponds to the formula:

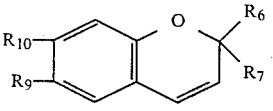

where $R_9$ is alkyl and $R_{10}$ is alkoxy.

19. The compound as in claim 11 wherein the active juvenile hormone corresponds to the formula:

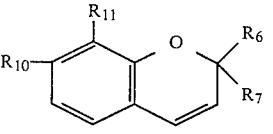

where $R_{10}$ is alkoxy and $R_{11}$ is alkyl.

20. The compound as in claims 14, 15, 16, 17, 18 or 19 wherein $R_6$ and $R_7$ are methyl.

21. The method of claim 1 where the compound is 5-methyl-7-ethoxy-2,2-dimethyl-3-chromene.

* * * * *